US00PP11774P2

(12) United States Plant Patent
Rother

(10) Patent No.: US PP11,774 P2
(45) Date of Patent: Feb. 13, 2001

(54) ARGYRANTHEMUM PLANT NAMED 'LEMON DELIGHT'

(76) Inventor: Reinhard W. Rother, 56 Emerald Monbulk Road, Emerald, Victoria, 3782 (AU)

( * ) Notice: Under 35 U.S.C. 154(b), the term of this patent shall be extended for 0 days.

(21) Appl. No.: 09/263,150

(22) Filed: Mar. 5, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Marguerite Daisy plant named Lemon Delight, characterized by its rounded, spreading and mounding plant habit; compact; freely branching, dense and bushy plants with short internodes and numerous leaves; freely flowering with numerous inflorescences per plant held beyond the foliage; large single-type inflorescences; lemon yellow ray florets and dark yellow disc florets; and high temperature and humidity tolerance.

1 Drawing Sheet

BACKGROUND OF THE INVENTION

The present invention relates to a new and distinct cultivar of Marguerite Daisy plant, botanically known as *Argyranthemum frutescens* and referred to by the cultivar name Lemon Delight.

The new cultivar is a product of a planned breeding program conducted by the Inventor in Emerald, Victoris, Australia. The objective of the breeding program was to develop new Marguerite Daisies that are heat-tolerant.

The new cultivar originated from a cross made by the Inventor in 1994 of the *Argyranthemum frutescens* cultivar Frosty, not patented, as the male or pollen parent, with the *Argyranthemum frutescens* cultivar Harvest Snow, not patented, as the female or seed parent. The cultivar Lemon Delight was discovered and selected by the Inventor as a flowering plant within the progeny of the stated cross in a controlled environment in Emerald, Victoria, Australia.

Plants of the new Marguerite Daisy are different from plants of the male parent, the cultivar Frosty, in growth habit, inflorescence color and size and tolerance to high temperatures and humidity.

Plants of the new Marguerite Daisy are different from plants of the female parent, the cultivar Harvest Snow, in growth habit, leaf color and size, and inflorescence color and size.

Asexual propagation of the new cultivar by terminal cuttings in Emerald, Victoria, Australia, has shown that the unique features of this new Marguerite Daisy are stable and are reproduced true to type in successive propagations.

SUMMARY OF THE INVENTION

The new Marguerite Daisy has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Lemon Delight' which distinguish 'Lemon Delight' as a new and distinct cultivar:

1. Rounded, spreading and mounding plant habit; compact; freely branching, dense and bushy plants with short internodes and numerous leaves.
2. Freely flowering with numerous inflorescences per plant held beyond the foliage.
3. Large single-type inflorescences.
4. Lemon yellow ray florets and dark yellow disc florets.
5. High temperature and humidity tolerance.

Plants of the new Marguerite Daisy can be compared to plants of the nonpatented commercial cultivar Harvest Gold. In side-by-side comparisons conducted in Emerald, Victoria, Australia, plants of the new Marguerite Daisy have lighter green leaves, lighter yellow ray florets and are more high temperature and humidity tolerant than plants of the cultivar Harvest Gold.

Plants of the new Marguerite Daisy can also be compared to plants of the cultivar Midas Gold (U.S. Plant patent application Ser. No. 09/263,151). In side-by-side comparisons conducted in Emerald, Victoria, Australia, plants of the new Marguerite Daisy are different from plants of the cultivar Midas Gold in ray and disc floret color and leaf shape.

BRIEF DESCRIPTION OF THE PHOTOGRAPHS

The accompanying colored photographs illustrate the overall appearance of the new cultivar, showing the colors as true as it is reasonably possible to obtain in colored reproductions of this type .

The photograph at the top of the sheet comprises a top perspective view of three typical plants of 'Lemon Delight' in a 25-cm container.

The photograph at the bottom of the sheet comprises close-up views of developing inflorescences (top) and mature and young leaves (bottom). Floret and foliage colors in the photographs may appear different from the actual colors due to light reflectance.

DETAILED BOTANICAL DESCRIPTION

The following observations, measurements and values describe a 25-cm container of three plants of the new Marguerite Daisy grown in Bonsall, Calif., in full sun with day temperatures ranging from 18 to 38° C. and night temperatures ranging from 13 to 18° C.

Color references are made to The Royal Horticultural Society Colour Chart except where general terms of ordinary dictionary significance are used.

Botanical classification: *Argyranthemum frutescens* cultivar Lemon Delight.

Parentage:

*Male or pollen parent.*—*Argyranthemum frutescens* cultivar Frosty, not patented.

*Female or seed parent.*—*Argyranthemum frutescens* cultivar Harvest Snow, not patented.

Propagation:

*Type.*—Terminal cuttings.

*Time to initiate roots.*—About 15 to 18 days at a temperatures of 22 to 25° C.

*Time to develop roots.*—About 25 to 28 days at a temperatures of 22 to 25° C.

*Rooting habit.*—Numerous, fine, and freely branching.

Plant description:

*General appearance.*—Rounded, spreading, bushy and mounding plant habit. Short internodes and numerous leaves result in a compact, dense and full plant habit. Pinnatifid foliage. Flexible wiry flower stems hold the inflorescences beyond the foliage; inflorescences occasionally appear to cascade. Appropriate for various sizes and types of containers.

*Crop time.*—About 8 to 12 weeks are required to produce a finished flowering plant in a 10-cm container from a rooted cutting.

*Plant height.*—About 25 cm from soil level to top of inflorescences.

*Plant width.*—About 30 to 40 cm.

*Branching.*—Freely branching; about seven or eight primary lateral branches with about three or four secondary laterals.

*Vigor.*—Vigorous.

*Lateral branches.*—Length: About 28 to 30 cm. Diameter: About 5 mm. Internode length: About 5 mm. Texture: Glabrous; primary laterals, woody at base.

*Stem color.*—Green, 144B, no anthocyanin.

*Foliage description.*—Arrangement: Alternate, single. Quantity of leaves per lateral branch: Numerous, about 26 per primary lateral, and about 35 per secondary lateral. Shape: Pinnatifid. Apex: Three-parted. Base: Attenuate; clasping; sessile. Margin: Seven-lobed; deeply incised. Length: About 8 cm. Width: About 4.5 cm. Texture: Glabrous and smooth. Durability to stresses: Good, very durable. Leaves have a waxy cuticle that resists water loss. Color: Young leaves, upper surface: 138A. Young leaves, lower surface: Slightly lighter than 138A. Mature leaves, upper surface: 137A; 143A towards stem. Mature leaves, lower surface: 137B. Venation, upper surface: 138B. Venation, lower surface: 137C.

Flowering description:

*Flowering habit.*—Inflorescences on wiry and flexible peduncles held beyond the foliage. Flat, single-type composite inflorescence form. Inflorescences form at upper leaf axils. Florets arranged acropetally on a capitulum. Inflorescences last about one week. Inflorescences persistent.

*Quantity of inflorescences.*—Freely flowering; typically about 12 inflorescences and buds per lateral stem; usually about 50 inflorescences and buds per plant.

*Natural flowering season.*—Natural flowering season is spring to early fall. Plants flower continuously during this period.

*Inflorescence size.*—Diameter: About 4.5 cm. Depth (height): About 1 cm. Disc diameter: About 1.2 cm.

*Frangrance.* —None.

*Fay florets.*—Aspect: Flat; with subsequent development, florets tend to reflex. Quantity per inflorescence and arrangement: About 19 ray florets arranged in a single whorl. Shape: Ligulate. Apex: Irregularly tri-dentate. Base: Attenuate. Margin: Entire. Length, outer florets: About 2.2 cm. Width, outer florets: About 5 mm. Texture: Smooth, soft, satiny. Color: When opening, upper surface: 3C. When opening, lower surface: 4D. Fully opened, upper surface: 4C; fading to 4D with subsequent development. Fully opened, lower surface: 4D.

*Disc florets.*—Shape: Tubular; 5-lobed. Quantity per inflorescence: About 134. Disc floret length: About 6 mm. Disc floret width: About 2 mm. Color: Immature: 145C; 5A at apex. Mature: 145C; 5A to 12A at apex.

*Phyllaries.*—Quantity per inflorescence and arrangement: About 22 per inflorescence; imbricate in three whorls; tightly pressed to the receptacle. Aspect: Cupped. Shape: Elliptic. Apex: Acute. Margin: Entire, outer edges slightly membranous. Texture: Smooth. Length: About 6 mm. Color: Upper surface: 145C. Lower surface: 138A.

*Peduncle.*—Length, first peduncle: About 5 cm. Length, fourth peduncle: About 5.5 cm. Strength: Wiry, flexible, inflorescences held beyound the foliage and occasionally appear to cascade. Angle: Upright to a 45° angle to the stem. Texture: Smooth. Color: 144A.

*Inflorescence bud.*—Shape: Ovoid. Length: About 1 cm. Diameter: About 7 mm. Color: 3C.

*Reproductive structures.*—Androecium: Stamens: About five. Anther shape: Oblong. Anther size: About 1 mm. Anther color: 9A. Pollen amount: Scarce. Pollen color: 9A. Gynoecium: Pistil number: One per floret. Pistil length: About 2 mm. Style length: About 1 mm. Style color: 5C. Stigma shape: Bilobate. Stigma color: 5A. Ovary color: 145A.

*Seed development.*—Seed production has not been observed.

Disease resistance: Resistance to pathogens common to Argyranthemum has not been observed.

Weather tolerance: Plants of the new Marguerite Daisy have demonstrated good tolerance to high temperature and high humidity conditions.

It is claimed:

1. A new and distinct Marguerite Daisy plant named 'Lemon Delight', as illustrated and described.

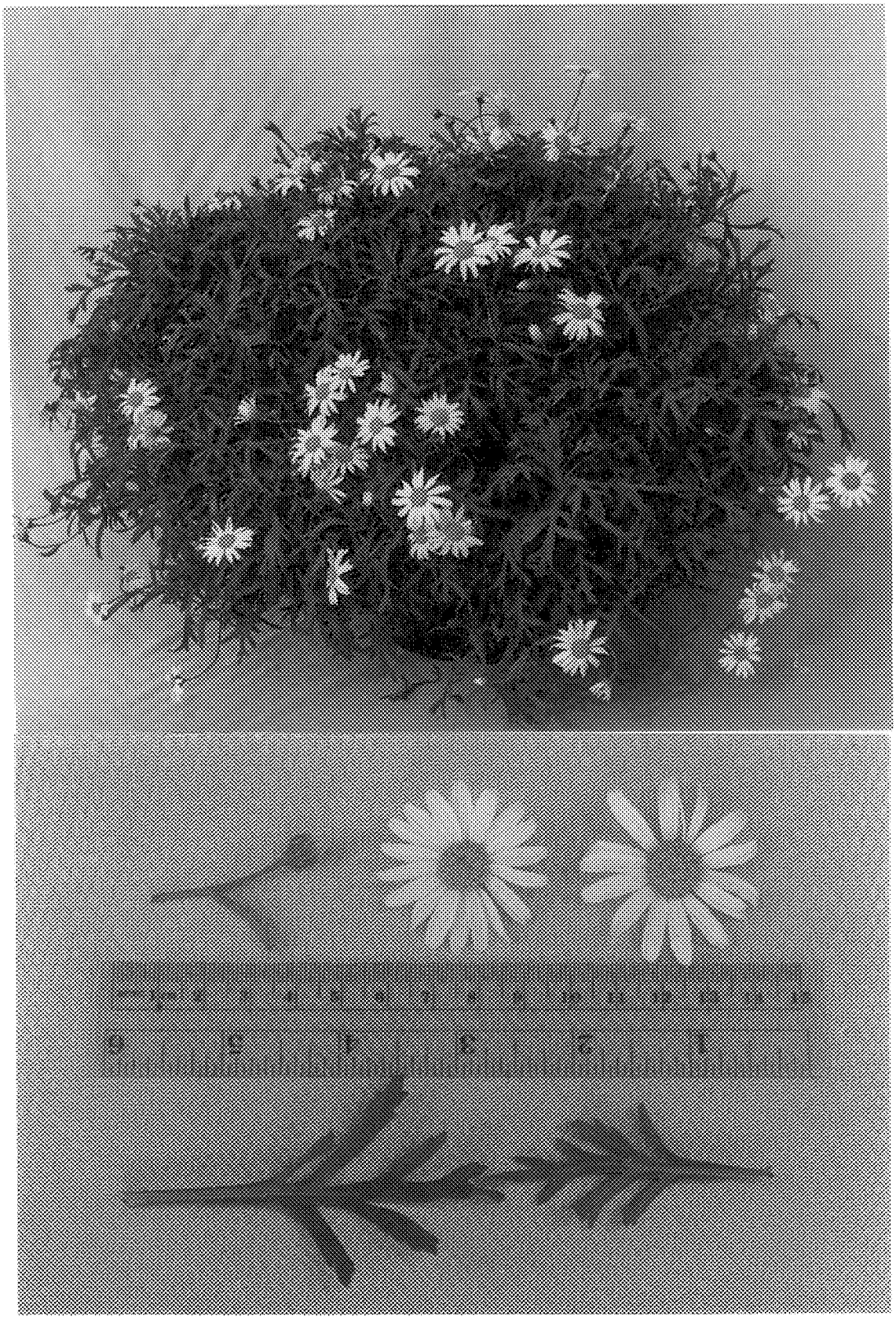

* * * * *